United States Patent
Fracassi et al.

(10) Patent No.: US 10,588,871 B1
(45) Date of Patent: Mar. 17, 2020

(54) TRANSDERMAL FORMULATION FOR THE TREATMENT OF PAIN AND/OR INFLAMMATION

(71) Applicant: NEXZOL PHARMA, INC., San Clemente, CA (US)

(72) Inventors: Joseph M. Fracassi, San Clemente, CA (US); Thomas J. Scarlata, San Clemente, CA (US)

(73) Assignee: NEXZOL PHARMA, INC., San Clemente, CA (US)

( * ) Notice: Subject to any disclaimer, the term of this patent is extended or adjusted under 35 U.S.C. 154(b) by 0 days.

(21) Appl. No.: 16/457,746

(22) Filed: Jun. 28, 2019

(51) Int. Cl.
| | | |
|---|---|---|
| *A61K 9/70* | (2006.01) | |
| *A61K 9/107* | (2006.01) | |
| *A61K 9/00* | (2006.01) | |
| *A61K 31/05* | (2006.01) | |
| *A61K 36/185* | (2006.01) | |
| *A61K 47/18* | (2017.01) | |
| *A61K 47/58* | (2017.01) | |
| *A61K 47/36* | (2006.01) | |
| *A61K 9/50* | (2006.01) | |
| *A61K 9/06* | (2006.01) | |
| *A61P 37/02* | (2006.01) | |
| *A61K 9/127* | (2006.01) | |

(52) U.S. Cl.
CPC ............ *A61K 31/05* (2013.01); *A61K 9/0014* (2013.01); *A61K 9/06* (2013.01); *A61K 9/127* (2013.01); *A61K 9/5005* (2013.01); *A61K 47/183* (2013.01); *A61K 47/36* (2013.01); *A61K 47/58* (2017.08); *A61P 37/02* (2018.01)

(58) Field of Classification Search
CPC .......... A61K 31/05; A61K 47/58; A61K 9/06; A61K 9/127; A61K 37/02; A61K 47/183
See application file for complete search history.

(56) References Cited

U.S. PATENT DOCUMENTS

| | | | |
|---|---|---|---|
| 9,375,417 B2 | 6/2016 | Smith et al. | |
| 9,533,942 B2 | 1/2017 | Stinchcomb et al. | |
| 10,028,919 B2 | 7/2018 | Kaufman | |
| 10,172,809 B2 | 1/2019 | Aung-Din | |
| 2011/0052694 A1 | 3/2011 | Stinchcomb et al. | |
| 2012/0308648 A1* | 12/2012 | Simes ...................... | A61K 9/06 424/450 |
| 2015/0126595 A1* | 5/2015 | Smith .................. | A61K 31/353 514/454 |
| 2016/0256410 A1 | 9/2016 | Aung-Din | |
| 2016/0256411 A1 | 9/2016 | Aung-Din | |
| 2016/0338974 A1 | 11/2016 | Aung-Din | |
| 2017/0000744 A1 | 1/2017 | Kaufman | |
| 2017/0266128 A1 | 9/2017 | Aung-Din | |
| 2018/0049994 A1 | 2/2018 | Aung-Din | |
| 2018/0055782 A1 | 3/2018 | Kaufman | |
| 2018/0214399 A1 | 8/2018 | Spector et al. | |
| 2018/0296631 A1 | 10/2018 | Radisic et al. | |
| 2018/0318237 A1 | 11/2018 | Aung-Din | |
| 2019/0083387 A1 | 3/2019 | Aung-Din | |
| 2019/0216870 A1* | 7/2019 | Witowski .................. | A23L 2/56 |

FOREIGN PATENT DOCUMENTS

| | | |
|---|---|---|
| EP | 2 473 475 B1 | 7/2012 |
| WO | WO 03101357 * | 12/2003 |
| WO | WO-2011/026144 A1 | 3/2011 |
| WO | WO-2016/100228 A2 | 6/2016 |
| WO | WO-2016/141056 A1 | 9/2016 |
| WO | WO-2016/144376 A1 | 9/2016 |
| WO | WO-2017/147691 A1 | 9/2017 |
| WO | WO-2018/035212 A1 | 2/2018 |
| WO | WO-2018/085794 A1 | 5/2018 |
| WO | WO-2018/140687 A1 | 8/2018 |

* cited by examiner

*Primary Examiner* — Mina Haghighatian
(74) *Attorney, Agent, or Firm* — Foley & Lardner LLP (57) ABSTRACT

Described herein are transdermal formulations of phytocannabinoids and methods of using the same in the treatment of pain and/or inflammation.

12 Claims, 6 Drawing Sheets

TRANSDERMAL FORMULATION FOR THE TREATMENT OF PAIN AND/OR INFLAMMATION

BACKGROUND

The present technology relates generally to the field of transdermal formulations for the treatment of pain.

SUMMARY

In one aspect, provided herein is a transdermal formulation comprising about 0.05% w/w to about 50% w/w phytocannabinoid dispersed in a pharmaceutically acceptable carrier comprising:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water.

In some embodiments, the formulation is a topical formulation. In some embodiments, the topical formulation is a semi-solid formulation selected from a gel, a lotion, a cream, an ointment, a serum, or a foam.

In some embodiments, the phytocannabinoid is selected from cannabidiol (CBD), cannabigerol (CBG), cannabichromene (CBC), cannabinol (CBN), cannabitriol (CBT), cannabidiolic acid (CBDA), cannabigerolic acid (CBGA), cannabidivarin (CBDV), beta caryophyllene, and tetrahydrocannabinol, or any combination thereof. In some embodiments, the cannabidiol is microencapsulated cannabidiol. In some embodiments, the microencapsulated cannabidiol comprises cannabidiol encapsulated within liposomes.

In some embodiments, the penetration enhancer comprises diethylene glycol monoethyl ether, lauryl alcohol, dimethyl sulfoxide (DMSO), dimethyl acetamide, N-methyl pyrrolidone, oleic acid, azone, oxazolidinone derivative, urea, terpene, or any combination thereof.

In some embodiments, the thickening agent comprises a cross-linked polyacrylic acid polymer; a cellulose derivative; xanthan gum, locust beam gum, guar gum or derivative thereof alginic acid; inorganic polymer; PEMULEN™ (a copolymer of acrylic acid and C10-C30 alkyl acrylate cross-linked with allyl pentaerythritol); or any combination thereof.

In some embodiments, the buffering agent comprises triethanolamine, potassium hydroxide, cocoamidodiethylamine, or any combination thereof.

In some embodiments, the sequestering agent comprises EDTA, or a salt and/or solvate thereof citric acid; tartaric acid; or any combination thereof.

In some embodiments, the preservative comprises phenoxyethanol, a urea derivative, ethylhexylglycerine, hydantoin, benzoic, sorbic acid, anisic acid, or any combination thereof.

In one aspect, provided herein is a transdermal formulation consisting of microencapsulated cannabidiol dispersed in a pharmaceutically acceptable carrier consisting of deionized water, a penetration enhancer, a thickening agent, a buffering agent, a sequestering agent, and a preservative. In some embodiments, the formulation is topical formulation. In some embodiments, the topical formulation is a semi-solid formulation selected from a gel, a lotion, a cream, an ointment, a serum, or a foam. In some embodiments, the formulation consists of about 0.20% w/w cannabidiol, about 18% w/w diethylene glycol monoethyl ether, about 1% w/w cross-linked polyacrylic acid polymer, about 0.3% w/w triethanolamine, about 0.5% w/w phenoxyethanol, about 0.05% w/w disodium EDTA dihydrate, and q.s. deionized water; wherein the cannabidiol is microencapsulated cannabidiol.

In another aspect, provided herein is a method of treating musculoskeletal pain and/or inflammation in a subject in need thereof, the method comprising topically administering to one or more regions of skin on the subject a therapeutically effective amount of a transdermal formulation described herein. In some embodiments, the transdermal formulation is administered by topical application to the region of skin on the subject without microneedle delivery. In some embodiments, the transdermal formulation is administered once every hour for an initial period of three hours for a total of four applications and then subsequently administered 3-4 times per day. In some embodiments, the musculoskeletal pain and/or inflammation is located at one or more of the foot, ankle, knee, hip, hand, wrist, elbow, neck, scalp, back, chest, abdomen, shoulder, arm, or leg, of the subject.

In another aspect, provided herein is a method for relieving pain associated with osteoarthritis of one or more joints in a subject in need thereof, the method comprising topically administering a therapeutically effective amount of a transdermal formulation described herein to one or more regions of skin covering the one or more joints on the subject. In some embodiments, the one or more joints are located at one or more of the foot, ankle, knee, hip, hand, wrist, elbow, neck, back, or shoulder of the subject. In some embodiments, the transdermal formulation is administered by topical application to the region of skin on the subject without microneedle delivery. In some embodiments, the transdermal formulation is administered once every hour for an initial period of three hours for a total of four applications and then subsequently administered 3-4 times per day.

In some embodiments, the formulation exhibits a lag effect wherein, following four consecutive hourly applications of the formulation to skin, the amount of cannabidiol delivered through the skin after 21 hours is greater than the amount delivered through the skin after 5 hours, as assessed in an in vitro permeation study using human cadaver skin.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "subject" refers to an animal, such as a mammal (including a human), that has been or will be the object of treatment, observation or experiment. "Subject" and "patient" may be used interchangeably, unless otherwise indicated. Mammals include, but are not limited to, mice, rodents, rats, simians, humans, farm animals, dogs, cats, sport animals, and pets. The methods described herein may be useful in human therapy and/or veterinary applications. In some embodiments, the subject is a mammal. In some embodiments, the subject is a human.

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease or disorder, or the manner of administration as determined by a qualified prescriber or caregiver.

The term "treatment" or "treating" means administering a formulation disclosed herein for the purpose of: (i) delaying the onset of a disease/disorder, that is, causing the clinical symptoms of the disease/disorder not to develop or delaying the development thereof; (ii) inhibiting the disease/disorder, that is, arresting the development of clinical symptoms; and/or (iii) relieving the disease/disorder, that is, causing the regression of clinical symptoms or the severity thereof.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. A pharmaceutically acceptable salt of an active agent can be used instead of the free base form of the active agent in any formulation disclosed herein.

As used herein, the term "musculoskeletal" refers to joints, tendons, ligaments, skeletal muscles (e.g., muscles that contract to pull on tendons and move the bones of the skeleton, maintain posture and body position, support soft tissues, guard entrances and exits to the digestive and urinary tracts; and maintain body temperature), nerves, and cartilage. Accordingly, in some embodiments, musculoskeletal pain/inflammation is located at one or more joints, tendons, ligaments, skeletal muscles, nerves, and cartilage.

As used herein, the term "transdermal" refers to topical application to a skin surface for local and/or systemic effect(s) depending on the active agent in the formulation.

Unless defined otherwise, all technical and scientific terms used herein have the same meaning as commonly understood by one of ordinary skill in the art to which this present invention belongs. Although any methods and materials similar or equivalent to those described herein can also be used in the practice or testing of the present invention, representative illustrative methods and materials are described herein.

Transdermal Formulations

In one aspect, provided herein are transdermal formulations comprising, consisting essentially of, or consisting of about 0.05% w/w to about 50% w/w synthetic or natural phytocannabinoid and pharmaceutically acceptable excipients.

In another aspect, provided herein are transdermal formulations comprising, consisting essentially of, or consisting of about 0.05% w/w to about 50% w/w synthetic or natural phytocannabinoid dispersed in a pharmaceutically acceptable carrier comprising, consisting essentially of, or consisting of:
  about 3% w/w to about 30% w/w penetration enhancer,
  about 0.8% w/w to about 1.3% w/w thickening agent,
  about 0.25% w/w to about 6% w/w buffering agent,
  about 0.05% w/w to about 0.08% w/w sequestering agent,
  about 0.4% w/w to about 0.8% w/w of preservative, and
  up to about 95.45% w/w of deionized water.

In another aspect, provided herein are transdermal formulations comprising, consisting essentially of, or consisting of about 0.05% w/w to about 50% w/w synthetic phytocannabinoid dispersed in a pharmaceutically acceptable carrier comprising, consisting essentially of, or consisting of:
  about 3% w/w to about 30% w/w penetration enhancer,
  about 0.8% w/w to about 1.3% w/w thickening agent,
  about 0.25% w/w to about 6% w/w buffering agent,
  about 0.05% w/w to about 0.08% w/w sequestering agent,
  about 0.4% w/w to about 0.8% w/w of preservative, and
  up to about 95.45% w/w of deionized water.

In another aspect, provided herein are transdermal formulations comprising, consisting essentially of, or consisting of about 0.05% w/w to about 50% w/w natural phytocannabinoid dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water.

In another aspect, provided herein are transdermal formulations comprising, consisting essentially of, or consisting of about 0.05% w/w to about 50% w/w hemp-derived phytocannabinoid dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water.

In another aspect, provided herein are transdermal formulations comprising, consisting essentially of, or consisting of about 0.05% w/w to about 50% w/w cannabidiol dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water.

In another aspect, provided herein are transdermal formulations comprising, consisting essentially of, or consisting of about 0.05% w/w to about 50% w/w cannabidiol dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water;
wherein the cannabidiol is microencapsulated cannabidiol.

In another aspect, provided herein are transdermal formulations comprising, consisting essentially of, or consisting of about 0.05% w/w to about 30% w/w cannabidiol dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water;
wherein the cannabidiol is microencapsulated cannabidiol.

In another aspect, provided herein are transdermal formulations comprising, consisting essentially of, or consisting of about 0.05% w/w to about 10% w/w cannabidiol dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water;
wherein the cannabidiol is microencapsulated cannabidiol.

In another aspect, provided herein are transdermal formulations comprising, consisting essentially of, or consisting of about 0.05% w/w to about 5% w/w cannabidiol dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water;
wherein the cannabidiol is microencapsulated cannabidiol.

In another aspect, provided herein are transdermal formulations comprising, consisting essentially of, or consisting of about 0.05% w/w to about 1% w/w cannabidiol dispersed in a pharmaceutically acceptable carrier comprising, consisting essentially of, or consisting of:
about 3% w/w to about 30% w/w penetration enhancer,
about 0.8% w/w to about 1.3% w/w thickening agent,
about 0.25% w/w to about 6% w/w buffering agent,
about 0.05% w/w to about 0.08% w/w sequestering agent,
about 0.4% w/w to about 0.8% w/w of preservative, and
up to about 95.45% w/w of deionized water;
wherein the cannabidiol is microencapsulated cannabidiol.

In another aspect, provided herein are transdermal formulations comprising, consisting essentially of, or consisting of microencapsulated cannabidiol dispersed in a pharmaceutically acceptable carrier comprising, consisting essentially of, or consisting of deionized water, a penetration enhancer, a thickening agent, a buffering agent, a sequestering agent, and a preservative.

In another aspect, provided herein are transdermal formulations consisting of
about 0.2% w/w cannabidiol,
about 18% w/w diethylene glycol monoethyl ether,
about 1% w/w cross-linked polyacrylic acid polymer,
about 0.3% w/w triethanolamine,
about 0.5% w/w phenoxyethanol,
about 0.05% w/w disodium EDTA dihydrate, and
q.s. deionized water;
wherein the cannabidiol is microencapsulated cannabidiol.

In any embodiments, the formulation disclosed herein may be in the form of a topical formulation. Topical formulations include, but are not limited to, gels, lotions, creams, ointments, pastes, serums, foams, sprays, powders, or liquids (e.g., suspension or solution). In any embodiments, the topical formulation may be a semi-solid formulation. A semi-solid formulation includes, but is not limited to, a gel, a lotion, a cream, an ointment, a suspension, a paste, a serum, and a foam.

In any embodiments, the formulation disclosed herein may be in the form of a lotion, cream, gel, paste, serum, or ointment. In some embodiments, the formulation disclosed herein is a gel.

Phytocannabinoid

The phytocannabinoid may be selected from one or more of cannabidiol (CBD), cannabigerol (CBG), cannabichromene (CBC), cannabinol (CBN), cannabitriol (CBT), cannabidiolic acid (CBDA), cannabigerolic acid (CBGA), cannabidivarin (CBDV), beta caryophyllene, and tetrahydrocannabinol. In some embodiments, the phytocannabinoid is cannabidiol (CBD). In some embodiments, the phytocannabinoid is cannabigerol (CBG). In some embodiments, the phytocannabinoid is cannabichromene (CBC). In some embodiments, the phytocannabinoid is cannabinol (CBN). In some embodiments, the phytocannabinoid is cannabitriol (CBT). In some embodiments, phytocannabinoid is cannabidiolic acid (CBDA). In some embodiments, the phytocannabinoid is cannabigerolic acid (CBGA). In some embodiments, the phytocannabinoid is cannabidivarin (CBDV). In some embodiments, the phytocannabinoid is beta caryophyllene. In some embodiments, the phytocannabinoid is tetrahydrocannabinol. In some embodiments, the phytocannabinoid excludes tetrahydrocannabinol.

In any of these embodiments, the phytocannabinoid may be synthetic or natural. As used herein, a "natural phytocannabinoid" refers to a phytocannabinoid isolated from a natural source, such as a plant. As used herein, a "synthetic phytocannabinoid" refers to a phytocannabinoid prepared synthetically. In some embodiments, the natural phytocannibinoid is a hemp-derived phytocannabinoid.

In any of these embodiments, the phytocannabinoid may be microencapsulated. In some embodiments, the microencapsulated phytocannabinoid comprises, consists essentially of, or consists of phytocannabinoid encapsulated within liposomes. In some embodiments, the phytocannabinoid is not microencapsulated.

In any embodiments, the phytocannabinoid may be present in the formulation disclosed herein in an amount of about 0.05% w/w to about 50% w/w. This includes about 0.05% w/w to about 45% w/w, about 0.05% w/w to about 40% w/w, about 0.05% w/w to about 35% w/w, about 0.05% w/w to about 30% w/w, about 0.05% w/w to about 25% w/w, about 0.05% w/w to about 20% w/w, about 0.05% w/w to about 15% w/w, about 0.05% w/w to about 10% w/w, about 0.05% w/w to about 5% w/w, about 0.05% w/w to about 4% w/w, about 0.05% w/w to about 3% w/w, about 0.05% w/w to about 2% w/w, about 0.05% w/w to about 1% w/w, about 0.05% w/w to about 0.5% w/w, about 0.1% w/w to about 45% w/w, about 0.1% w/w to about 40% w/w, about 0.1% w/w to about 35% w/w, about 0.1% w/w to about 30% w/w, about 0.1% w/w to about 25% w/w, about 0.1% w/w to about 20% w/w, about 0.1% w/w to about 15% w/w, about 0.1% w/w to about 10% w/w, about 0.1% w/w to about 5% w/w, about 0.1% w/w to about 4% w/w, about 0.1% w/w to about 3% w/w, about 0.1% w/w to about 2% w/w, about 0.1% w/w to about 1% w/w, about 0.1% w/w to about 0.5% w/w, about 1% w/w to about 45% w/w, about 1% w/w to about 40% w/w, about 1% w/w to about 35% w/w, about 1% w/w to about 30% w/w, about 1% w/w to about 25% w/w, about 1% w/w to about 20% w/w, about 1% w/w to about 15% w/w, about 1% w/w to about 10% w/w, about 1% w/w to about 5% w/w, about 5% w/w to about 45% w/w, about 5% w/w to about 40% w/w, about 5% w/w to about 35% w/w, about 5% w/w to about 30% w/w, about 5% w/w to about 25% w/w, about 5% w/w to about 20% w/w, about 5% w/w to about 15% w/w, about 5% w/w to about 10% w/w, 10% w/w to about 50% w/w, 10% w/w to about 45% w/w, about 10% w/w to about 40% w/w, about 10% w/w to about 35% w/w, about 10% w/w to about 30% w/w, about 10% w/w to about 25% w/w, about 10% w/w to about 20% w/w, and about 10% w/w to about 15% w/w. Thus, the phytocannabinoid may be present in the formulation disclosed herein in an amount of about 0.05, 0.06, 0.07, 0.08, 0.09, 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% w/w, including increments therein.

In any embodiments, the phytocannabinoid may be present in the formulation disclosed herein in an amount of about 50 mg to about 500 mg. This includes about 50 mg to about 100 mg, 50 mg to about 125 mg, 50 mg to about 150 mg, 50 mg to about 175 mg, 50 mg to about 200 mg, 50 mg to about 225 mg, 50 mg to about 250 mg, 50 mg to about 275 mg, 50 mg to about 300 mg, 50 mg to about 325 mg, 50 mg to about 350 mg, 50 mg to about 375 mg, 50 mg to about 400 mg, 50 mg to about 425 mg, 50 mg to about 450 mg, 50 mg to about 475 mg; 100 mg to about 125 mg, 100 mg to about 150 mg, 100 mg to about 175 mg, 100 mg to about 200 mg, 100 mg to about 225 mg, 100 mg to about 250 mg, 100 mg to about 275 mg, 100 mg to about 300 mg, 100 mg to about 325 mg, 100 mg to about 350 mg, 100 mg to about 375 mg, 100 mg to about 400 mg, 100 mg to about 425 mg, 100 mg to about 450 mg, 100 mg to about 475 mg, and 100 mg to about 500 mg. Thus, the phytocannabinoid may be present in the formulation disclosed herein in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg, including increments therein.

In any embodiments, the phytocannabinoid may be present in the formulation disclosed herein in an amount of about 1 mg/mL to about 500 mg/mL. This includes about 1 mg/mL to about 25 mg/mL; about 1 mg/mL to about 50 mg/mL; about 1 mg/mL to about 75 mg/mL; about 1 mg/mL to about 100 mg/mL, 1 mg/mL to about 125 mg/mL, 1 mg/mL to about 150 mg/mL, 1 mg/mL to about 175 mg/mL, 1 mg/mL to about 200 mg/mL, 1 mg/mL to about 225 mg/mL, 1 mg/mL to about 250 mg/mL, 1 mg/mL to about 275 mg/mL, 1 mg/mL to about 300 mg/mL, 1 mg/mL to about 325 mg/mL, 1 mg/mL to about 350 mg/mL, 1 mg/mL to about 375 mg/mL, 1 mg/mL to about 400 mg/mL, 1 mg/mL to about 425 mg/mL, 1 mg/mL to about 450 mg/mL, 1 mg/mL to about 475 mg/mL; about 25 mg/mL to about 50 mg/mL, about 25 mg/mL to about 75 mg/mL, about 25 mg/mL to about 100 mg/mL, 25 mg/mL to about 125 mg/mL, 25 mg/mL to about 150 mg/mL, 25 mg/mL to about 175 mg/mL, 25 mg/mL to about 200 mg/mL, 25 mg/mL to about 225 mg/mL, 25 mg/mL to about 250 mg/mL, 25 mg/mL to about 275 mg/mL, 25 mg/mL to about 300 mg/mL, 25 mg/mL to about 325 mg/mL, 25 mg/mL to about 350 mg/mL, 25 mg/mL to about 375 mg/mL, 25 mg/mL to about 400 mg/mL, 25 mg/mL to about 425 mg/mL, 25 mg/mL to about 450 mg/mL, 25 mg/mL to about 475 mg/mL; about 50 mg/mL to about 100 mg/mL, 50 mg/mL to about 125 mg/mL, 50 mg/mL to about 150 mg/mL, 50 mg/mL to about 175 mg/mL, 50 mg/mL to about 200 mg/mL, 50 mg/mL to about 225 mg/mL, 50 mg/mL to about 250 mg/mL, 50 mg/mL to about 275 mg/mL, 50 mg/mL to about 300 mg/mL, 50 mg/mL to about 325 mg/mL, 50 mg/mL to about 350 mg/mL, 50 mg/mL to about 375 mg/mL, 50 mg/mL to about 400 mg/mL, 50 mg/mL to about 425 mg/mL, 50 mg/mL to about 450 mg/mL, 50 mg/mL to about 475 mg/mL; 100 mg/mL to about 125 mg/mL, 100 mg/mL to about 150 mg/mL, 100 mg/mL to about 175 mg/mL, 100 mg/mL to about 200 mg/mL, 100 mg/mL to about 225 mg/mL, 100 mg/mL to about 250 mg/mL, 100 mg/mL to about 275 mg/mL, 100 mg/mL to about 300 mg/mL, 100 mg/mL to about 325 mg/mL, 100 mg/mL to about 350 mg/mL, 100 mg/mL to about 375 mg/mL, 100 mg/mL to about 400 mg/mL, 100 mg/mL to about 425 mg/mL, 100 mg/mL to about 450 mg/mL, 100 mg/mL to about 475 mg/mL, and 100 mg/mL to about 500 mg/mL. Thus, the active agent may be present in the formulation disclosed herein in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg/mL, including increments therein.

In some embodiments, the phytocannabinoid is or comprises cannabidiol, which may be present in the formulation disclosed herein in an amount of about 0.5% w/w to about 50% w/w. This includes about 0.05% w/w to about 45% w/w, about 0.05% w/w to about 40% w/w, about 0.05% w/w to about 35% w/w, about 0.05% w/w to about 30% w/w, about 0.05% w/w to about 25% w/w, about 0.05% w/w to about 20% w/w, about 0.05% w/w to about 15% w/w, about 0.05% w/w to about 10% w/w, about 0.05% w/w to about 5% w/w, about 0.05% w/w to about 4% w/w, about 0.05% w/w to about 3% w/w, about 0.05% w/w to about 2% w/w, about 0.05% w/w to about 1% w/w, about 0.05% w/w to about 0.5% w/w, about 0.1% w/w to about 45% w/w, about 0.1% w/w to about 40% w/w, about 0.1% w/w to about 35% w/w, about 0.1% w/w to about 30% w/w, about 0.1% w/w to about 25% w/w, about 0.1% w/w to about 20% w/w, about 0.1% w/w to about 15% w/w, about 0.1% w/w to about 10% w/w, about 0.1% w/w to about 5% w/w, about 0.1% w/w to about 4% w/w, about 0.1% w/w to about 3% w/w, about 0.1% w/w to about 2% w/w, about 0.1% w/w to about 1% w/w, about 0.1% w/w to about 0.5% w/w, about 1% w/w to about 45% w/w, about 1% w/w to about 40% w/w, about 1% w/w to about 35% w/w, about 1% w/w to about 30% w/w, about 1% w/w to about 25% w/w, about 1% w/w to about 20% w/w, about 1% w/w to about 15% w/w, about 1% w/w to about 10% w/w, about 1% w/w to about 5% w/w, about 5% w/w to about 45% w/w, about 5% w/w to about 40% w/w, about 5% w/w to about 35% w/w, about 5% w/w to about 30% w/w, about 5% w/w to about 25% w/w, about 5% w/w to about 20% w/w, about 5% w/w to about 15% w/w, about 5% w/w to about 10% w/w, 10% w/w to about 45% w/w, about 10% w/w to about 40% w/w, about 10% w/w to about 35% w/w, about 10% w/w to about 30% w/w, about 10% w/w to about 25% w/w, about 10% w/w to about 20% w/w, and about 10% w/w to about 15% w/w. In some embodiments, cannabidiol is present in the formulation disclosed herein in an amount of about 0.05, 0.06, 0.07, 0.08, 0.09, 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% w/w, including increments therein.

In some embodiments, the phytocannabinoid is or comprises cannabidiol, which may be present in the formulation disclosed herein in an amount of about 50 mg to about 500 mg. This includes about 50 mg to about 100 mg, 50 mg to about 125 mg, 50 mg to about 150 mg, 50 mg to about 175 mg, 50 mg to about 200 mg, 50 mg to about 225 mg, 50 mg to about 250 mg, 50 mg to about 275 mg, 50 mg to about 300 mg, 50 mg to about 325 mg, 50 mg to about 350 mg, 50 mg to about 375 mg, 50 mg to about 400 mg, 50 mg to about 425 mg, 50 mg to about 450 mg, 50 mg to about 475 mg; 100 mg to about 125 mg, 100 mg to about 150 mg, 100 mg to about 175 mg, 100 mg to about 200 mg, 100 mg to about 225 mg, 100 mg to about 250 mg, 100 mg to about 275 mg, 100 mg to about 300 mg, 100 mg to about 325 mg, 100 mg to about 350 mg, 100 mg to about 375 mg, 100 mg to about 400 mg, 100 mg to about 425 mg, 100 mg to about 450 mg, 100 mg to about 475 mg, and 100 mg to about 500 mg. In some embodiments, cannabidiol is present in the formulation disclosed herein in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg, including increments therein.

In any embodiments, the phytocannabinoid is or comprises cannabidiol, which may be present in the formulation disclosed herein in an amount of about 1 mg/mL to about 500 mg/mL. This includes about 1 mg/mL to about 25 mg/mL; about 1 mg/mL to about 50 mg/mL; about 1 mg/mL to about 75 mg/mL; about 1 mg/mL to about 100 mg/mL, 1 mg/mL to about 125 mg/mL, 1 mg/mL to about 150 mg/mL, 1 mg/mL to about 175 mg/mL, 1 mg/mL to about 200 mg/mL, 1 mg/mL to about 225 mg/mL, 1 mg/mL to about 250 mg/mL, 1 mg/mL to about 275 mg/mL, 1 mg/mL to about 300 mg/mL, 1 mg/mL to about 325 mg/mL, 1 mg/mL to about 350 mg/mL, 1 mg/mL to about 375 mg/mL, 1 mg/mL to about 400 mg/mL, 1 mg/mL to about 425 mg/mL, 1 mg/mL to about 450 mg/mL, 1 mg/mL to about 475 mg/mL; about 25 mg/mL to about 50 mg/mL, about 25 mg/mL to about 75 mg/mL, about 25 mg/mL to about 100 mg/mL, 25 mg/mL to about 125 mg/mL, 25 mg/mL to about 150 mg/mL, 25 mg/mL to about 175 mg/mL, 25 mg/mL to about 200 mg/mL, 25 mg/mL to about 225 mg/mL, 25 mg/mL to about 250 mg/mL, 25 mg/mL to about 275 mg/mL, 25 mg/mL to about 300 mg/mL, 25 mg/mL to about 325 mg/mL, 25 mg/mL to about 350 mg/mL, 25 mg/mL to about 375 mg/mL, 25 mg/mL to about 400 mg/mL, 25 mg/mL to about 425 mg/mL, 25 mg/mL to about 450 mg/mL, 25 mg/mL to about 475 mg/mL; about 50 mg/mL to about 100 mg/mL, 50 mg/mL to about 125 mg/mL, 50 mg/mL to about 150 mg/mL, 50 mg/mL to about 175 mg/mL, 50 mg/mL to about 200 mg/mL, 50 mg/mL to about 225 mg/mL, 50 mg/mL to about 250 mg/mL, 50 mg/mL to about 275 mg/mL, 50 mg/mL to about 300 mg/mL, 50 mg/mL to about 325 mg/mL, 50 mg/mL to about 350 mg/mL, 50 mg/mL to about 375 mg/mL, 50 mg/mL to about 400 mg/mL, 50 mg/mL to about 425 mg/mL, 50 mg/mL to about 450 mg/mL, 50 mg/mL to about 475 mg/mL; 100 mg/mL to about 125 mg/mL, 100 mg/mL to about 150 mg/mL, 100 mg/mL to about 175 mg/mL, 100 mg/mL to about 200 mg/mL, 100 mg/mL to about 225 mg/mL, 100 mg/mL to about 250 mg/mL, 100 mg/mL to about 275 mg/mL, 100 mg/mL to about 300 mg/mL, 100 mg/mL to about 325 mg/mL, 100 mg/mL to about 350 mg/mL, 100 mg/mL to about 375 mg/mL, 100 mg/mL to about 400 mg/mL, 100 mg/mL to about 425 mg/mL, 100 mg/mL to about 450 mg/mL, 100 mg/mL to about 475 mg/mL, and 100 mg/mL to about 500 mg/mL. Thus, the active agent may be present in the formulation disclosed herein in an amount of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg/mL, including increments therein.

In some embodiments, the cannabidiol is microencapsulated cannabidiol. In some embodiments, the microencapsulated cannabidiol comprises, consists essentially of, or consists of cannabidiol encapsulated within liposomes. Microencapsulated cannabidiol can be obtained through methods known in the art or from commercially available sources. One non-limiting example of a commercially available microencapsulated cannabidiol is CEBIDIOL™ (Isodiol International Inc.).

Penetration Enhancer

As noted above, the formulations described herein include a penetration enhancer. In some embodiments, the penetration enhancer is selected from diethylene glycol monoethyl ether, lauryl alcohol, dimethyl sulfoxide (DMSO), dimethyl acetamide, N-methyl pyrrolidone, oleic acid, azone, oxazolidinone derivatives, urea, terpenes (including, but not limited to, menthol, linalyl alcohol, eugenol, limonene, pinene, and squalene), or any combination thereof.

In some embodiments, the penetration enhancer comprises, consists essentially of, or consists of diethylene glycol monoethyl ether.

In some embodiments, the penetration enhancer is present in the formulation disclosed herein in an amount of about 3% w/w to about 30% w/w. This includes about 3% w/w to about 25% w/w, about 3% w/w to about 20% w/w, about 5% w/w to about 30% w/w, about 5% w/w to about 25% w/w, about 5% w/w to about 20% w/w, about 8% w/w to about 30% w/w, about 8% w/w to about 25% w/w, about 8% w/w to about 20% w/w, about 10% w/w to about 30% w/w, about 10% w/w to about 25% w/w, about 10% w/w to about 20% w/w, about 15% w/w to about 30% w/w, about 15% w/w to about 25% w/w, and about 15% w/w to about 20% w/w. In some embodiments, the penetration enhancer is present in the formulation disclosed herein in an amount of about 3, 4, 5, 6, 7, 8, 9, 10, 11, 12, 13, 14, 15, 16, 17, 18, 19, 20, 21, 22, 23, 24, 25, 26, 27, 28, 29, or 30% w/w, including increments therein. In some embodiments, the penetration enhancer is present in the formulation disclosed herein in an amount of about 18% w/w.

Thickening Agent

As noted above, the formulations described herein include a thickening agent. In some embodiments, the thickening agent is selected from a cross-linked polyacrylic acid polymer (e.g, a carbomer); a cellulose derivative (e.g., hydroxyethylcellulose, ethyl cellulose, hydroxypropyl cellulose, carboxymethyl cellulose, sodium carboxymethyl cellulose); xanthan gum, locust beam gum, guar gum or derivative thereof; alginic acid; inorganic polymer (such as Weegum, a silicate of aluminum and magnesium); PEMULEN™ (a copolymer of acrylic acid and C10-C30 alkyl acrylate cross-linked with allyl pentaerythritol); or any combination thereof.

In some embodiments, the thickening agent comprises, consists essentially of, or consists of a cross-linked polyacrylic acid polymer. In some embodiments, the cross-linked polyacrylic acid polymer is a carbomer. Commercial carbomers include, but are not limited to, CARBOPOL® polymers such as CARBOPOL® Ultrez 10 NF, CARBOPOL® Ultrez 20, CARBOPOL® ETD 2020 NF, CARBOPOL® 71G NF, CARBOPOL® 971P NF, CARBOPOL® 974P NF, CARBOPOL® 980 NF, CARBOPOL® 981 NF, and CARBOPOL® 5984 EP. CARBOPOL® Ultrez 10 NF and CARBOPOL® ETD 2020 NF are carbomer homopolymers or copolymers that contain a block copolymer of polyethylene glycol and a long chain alkyl acid ester.

In some embodiments, the thickening agent is present in the formulation disclosed herein in an amount of about 0.8% w/w to about 1.3% w/w. This includes about 0.8% w/w to about 1.2% w/w, about 0.8% w/w to about 1.1% w/w, about 0.8% w/w to about 1.0% w/w, about 0.9% w/w to about 1.3% w/w, about 0.9% w/w to about 1.2% w/w, about 0.9% w/w to about 1.1% w/w, about 1.0% w/w to about 1.3% w/w, and about 1.0% w/w to about 1.2% w/w. In some embodiments, the thickening agent is present in the formulation disclosed herein in an amount of about 0.8, 0.9, 1.0, 1.1, 1.2, or 1.3% w/w, including increments therein. In some embodiments, the thickening agent is present in the formulation disclosed herein in an amount of about 1% w/w.

Buffering Agent

As noted above, the formulations described herein include a buffering agent. In some embodiments, the buffering agent is selected from triethanolamine, sodium hydroxide, potassium hydroxide, cocoamidodiethylamine, or any combination thereof.

In some embodiments, the buffering agent comprises, consists essentially of, or consists of triethanolamine.

In some embodiments, the buffering agent is present in the formulation disclosed herein in an amount of about 0.25% w/w to about 6% w/w. This includes about 0.25% w/w to about 5% w/w, about 0.25% w/w to about 4% w/w, about 0.25% w/w to about 3% w/w, about 0.25% w/w to about 2% w/w, about 0.25% w/w to about 1% w/w, about 0.5% w/w to about 6% w/w, 0.5% w/w to about 5% w/w, about 0.5% w/w to about 4% w/w, about 0.5% w/w to about 3% w/w, about 0.5% w/w to about 2% w/w, and about 0.5% w/w to about 1% w/w. In some embodiments, the buffering agent is present in the formulation disclosed herein in an amount of about 0.25, 0.30, 0.35, 0.40, 0.45, 0.50, 0.55, 0.60, 0.65, 0.70, 0.75, 0.80, 0.85, 0.90, 0.95, 1.00, 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, or 6.00% w/w, including increments therein.

Sequestering Agent

As noted above, the formulations described herein include a sequestering agent. In some embodiments, the sequestering agent is selected from EDTA, or a salt and/or solvate thereof citric acid; tartaric acid; or any combination thereof.

In some embodiments, the sequestering agent comprises, consists essentially of, or consists of EDTA, or a salt and/or solvate thereof.

In some embodiments, the sequestering agent is present in the formulation disclosed herein in an amount of about 0.05% w/w to about 0.08% w/w. This includes about 0.05% w/w to about 0.07% w/w, about 0.06% w/w to about 0.08% w/w, about 0.06% w/w to about 0.07% w/w, and about 0.07% w/w to about 0.08% w/w. In some embodiments, the sequestering agent is present in the formulation disclosed herein in an amount of about 0.05, 0.055, 0.06, 0.065, 0.07, 0.075, or 0.08% w/w, including increments therein.

Preservative

As noted above, the formulations described herein include a preservative. In some embodiments, the preservative is selected from phenoxyethanol, urea derivatives (such as, but not limited to, diazolidinyl urea and imidazolidinyl urea), ethylhexylglycerine, hydantoin, benzoic, sorbic acid, anisic acid, or any combination thereof.

In some embodiments, the preservative comprises, consists essentially of, or consists of phenoxyethanol.

In some embodiments, the preservative is present in the formulation disclosed herein in an amount of about 0.4% w/w to about 0.8% w/w. This includes about 0.4% w/w to about 0.7% w/w, about 0.4% w/w to about 0.6% w/w, about 0.4% w/w to about 0.5% w/w, about 0.5% w/w to about 0.8% w/w, about 0.5% w/w to about 0.7% w/w, about 0.5% w/w to about 0.6% w/w, about 0.6% w/w to about 0.8% w/w, about 0.6% w/w to about 0.7% w/w, and about 0.7% w/w to about 0.8% w/w. In some embodiments, the preservative is present in the formulation disclosed herein in an amount of about 0.4, 0.45, 0.5, 0.55, 0.6, 0.65, 0.7, 0.75, or 0.8% w/w, including increments therein.

Other Components

The formulations described herein may include one or more other components suitable for use in a transdermal composition. Deionized water is added to the formulation as needed (q.s.). The formulations described herein comprise, consist essentially of, or consist of up to about 95.45% w/w deionized water. This includes about 11.82% w/w to about 95.45% w/w and ranges in between. In some embodiments, the formulation comprises, consists essentially of, or consists of 79.5% w/w deionized water.

The formulations described herein are alcohol-free. The term "alcohol-free" as it pertains to a formulation described herein means that the formulation is formulated without methanol, ethanol, iso-propanol, n-propanol, tert-butanol, n-butanol, and other alcohols of similarly low boiling point.

Delivery Profile

In some embodiments, the formulation disclosed herein exhibits a delivery profile that includes a lag effect wherein, following four consecutive hourly applications of the formulation to skin, the amount of phytocannabinoid delivered through the skin after 21 hours is greater than the amount delivered through the skin after 5 hours, as assessed in an in vitro permeation study using human cadaver skin. In some embodiments, the formulation disclosed herein exhibits a delivery profile that includes a lag effect wherein, following four consecutive hourly applications of the formulation to skin, the amount of cannabidiol delivered through the skin after 21 hours is greater than the amount delivered through the skin after 5 hours, as assessed in an in vitro permeation study using human cadaver skin.

In some embodiments, the formulation disclosed herein exhibits a lag effect wherein, following three consecutive hourly applications of the formulation to skin, the amount of phytocannabinoid delivered through the skin after 22 hours is greater than the amount delivered through the skin after 5 hours, as assessed in an in vitro permeation study using human cadaver skin. In some embodiments, the formulation disclosed herein exhibits a lag effect wherein, following three consecutive hourly applications of the formulation to skin, the amount of cannabidiol delivered through the skin after 22 hours is greater than the amount delivered through the skin after 5 hours, as assessed in an in vitro permeation study using human cadaver skin.

In some embodiments, the formulation transdermally delivers phytocannabinoid to skin in an amount of at least 15, 16, 17, 18, 19, 20, 21, 22, or 23 $\mu g/cm^2$ of skin, as assessed in an in vitro retention study using human cadaver skin after 24 hours following an initial application of the formulation to the skin. In some embodiments, the formulation transdermally delivers cannabidiol to skin in an amount of at least 15, 16, 17, 18, 19, 20, 21, 22, or 23 $\mu g/cm^2$ of skin, as assessed in an in vitro retention study using human cadaver skin after 24 hours following an initial application of the formulation to the skin.

Without being bound to any one particular theory, it is believed that lipophilicity of the formulation of the present technology is modulated such that phytocannabinoid in the formulation can permeate into the skin, accumulate within the skin, and then be delivered through the skin, thereby exhibiting a lag effect as described herein.

Methods of Treatment

In another aspect, provided herein are methods of treating pain and/or inflammation in a subject in need thereof, the methods comprising, consisting essentially of, or consisting of topically administering to one or more regions of skin on the subject a therapeutically effective amount of a transdermal formulation disclosed herein.

In another aspect, provided herein are methods of treating pain in a subject in need thereof, the methods comprising, consisting essentially of, or consisting of topically administering to one or more regions of skin on the subject a therapeutically effective amount of a transdermal formulation disclosed herein.

In another aspect, provided herein are methods of treating inflammation in a subject in need thereof, the methods comprising, consisting essentially of, or consisting of topically administering to one or more regions of skin on the subject a therapeutically effective amount of a transdermal formulation disclosed herein.

In another aspect, provided herein are methods of treating musculoskeletal pain and/or inflammation in a subject in need thereof, the methods comprising, consisting essentially of, or consisting of topically administering to one or more regions of skin on the subject a therapeutically effective amount of a transdermal formulation disclosed herein.

In some embodiments, the musculoskeletal pain and/or inflammation is located at one or more of the foot, ankle, knee, hip, hand, wrist, elbow, neck, scalp, back, chest, abdomen, shoulder, arm, or leg, of the subject.

In another aspect, provided herein are methods for relieving pain associated with osteoarthritis of one or more joints in a subject in need thereof, the methods comprising, consisting essentially of, or consisting of topically administering a therapeutically effective amount of a transdermal formulation disclosed herein to one or more regions of skin covering the one or more joints on the subject.

In some embodiments, the one or more joints are located at one or more of the foot, ankle, knee, hip, hand, wrist, elbow, neck, back, or shoulder of the subject.

In some embodiments, the transdermal formulation disclosed herein is administered by topical application to the region of skin on the subject without microneedle delivery.

In some embodiments, the transdermal formulation disclosed herein is administered once every hour for an initial period of two hours for a total of three applications and then subsequently administered 3-4 times per day. In some embodiments, the transdermal formulation disclosed herein is administered once every hour for an initial period of three hours for a total of four applications and then subsequently administered 3-4 times per day. In some embodiments, the transdermal formulation disclosed herein is administered once every hour for an initial period of four hours for a total of five applications and then subsequently administered 3-4 times per day.

Packaging

The formulations disclosed herein may be provided in any suitable container, such as a jar, a tube, or a container with a pump dispenser, optionally, a unit dose pump dispenser. In some embodiments, the formulation disclosed herein is provided in a container with a medical grade pump dispenser, optionally, a unit dose pump dispenser. In some embodiments, the formulation disclosed herein is provided in a container with a medical grade pump dispenser with a cooling tip, optionally, a unit dose pump dispenser.

The present invention, thus generally described, will be understood more readily by reference to the following examples, which are provided by way of illustration and are not intended to be limiting of the present invention.

EXAMPLES

| Example 1. Formulation of Cannabidiol (Formulation A100) | |
|---|---|
| Constituents | Concentration (% w/w) |
| cannabidiol* | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

*microencapsulated (CEBIDIOL ™), 100 mg CBD/50 mL composition

Example 2. Repeat Application Study—Permeation Assessment

General Protocol

Skin samples from suitable human donors shipped and stored frozen at −20° C. were used. The skins were removed from the freezer and allowed to equilibrate to room temperature. They were then punched with a steel punch to fit the top of the receptor cell. They were visually examined under stereoptic magnifier to confirm the absence of any skin defects. Receptor compartments were filled with the receptor fluid. Skin pieces were mounted on the receptor cells, the donor compartments were placed on top, and both compartments were clamped together. The skins were then allowed to hydrate in contact with the receptor fluid for ~1 hour. Any cells showing leakage were replaced.

Five replicates of each formulation were tested versus controls (e.g., composition of the present invention versus marketed formulation). Each test formulation was applied at a dose of 10 mg and spread uniformly over a skin sample of 0.55 cm². The Franz cells were maintained at 35° C. and the receptor compartment was continuously stirred with a magnetic stir bar. A sample was taken from each receptor compartment at predetermined time intervals (e.g., 2, 4, 6/8 and 22/24 hour). The samples were assayed by HPLC.

In this particular study, the set of cells was divided into 4 groups of 5 Franz cells. Approximately 10 mg of Formulation A100 was applied to the skin of each donor compartment of the cells. The skin was obtained from a human male (63 years old, 158 lbs, back skin, 500 μm thickness).

Formulation A100 application: The first group of (5) cells was treated as in Example 2 with no further formulation application.

Formulation A100 application +1 repeat application: In the second group of (5) cells, after 1 hour, the remaining formulation at the surface of the skin samples was first removed and the samples were further wiped and cleaned quickly with a cotton swab. Then, another application of approximately 10 mg of formulation was applied.

Formulation A100 application +2 repeat applications: In the third group of (5) cells, after each of 1 hour and 2 hours, the remaining formulation at the surface of the skin samples was first removed and the samples were further wiped and cleaned quickly with a cotton swab, and then further applications of approximately 10 mg of formulation were re-applied.

Formulation A100 application +3 repeat applications: In the fourth group of (5) cells, after each of 1 hour, 2 hours, and 3 hours, the remaining formulation at the surface of the skin samples was first removed and the samples were further wiped and cleaned quickly with a cotton swab, and then further applications of approximately 10 mg of formulation were re-applied.

A sample was taken from each receptor compartment at predetermined times (2, 4, 6, 8, and 24 hours) in all study groups. All samples were analyzed by HPLC.

Figure 1:
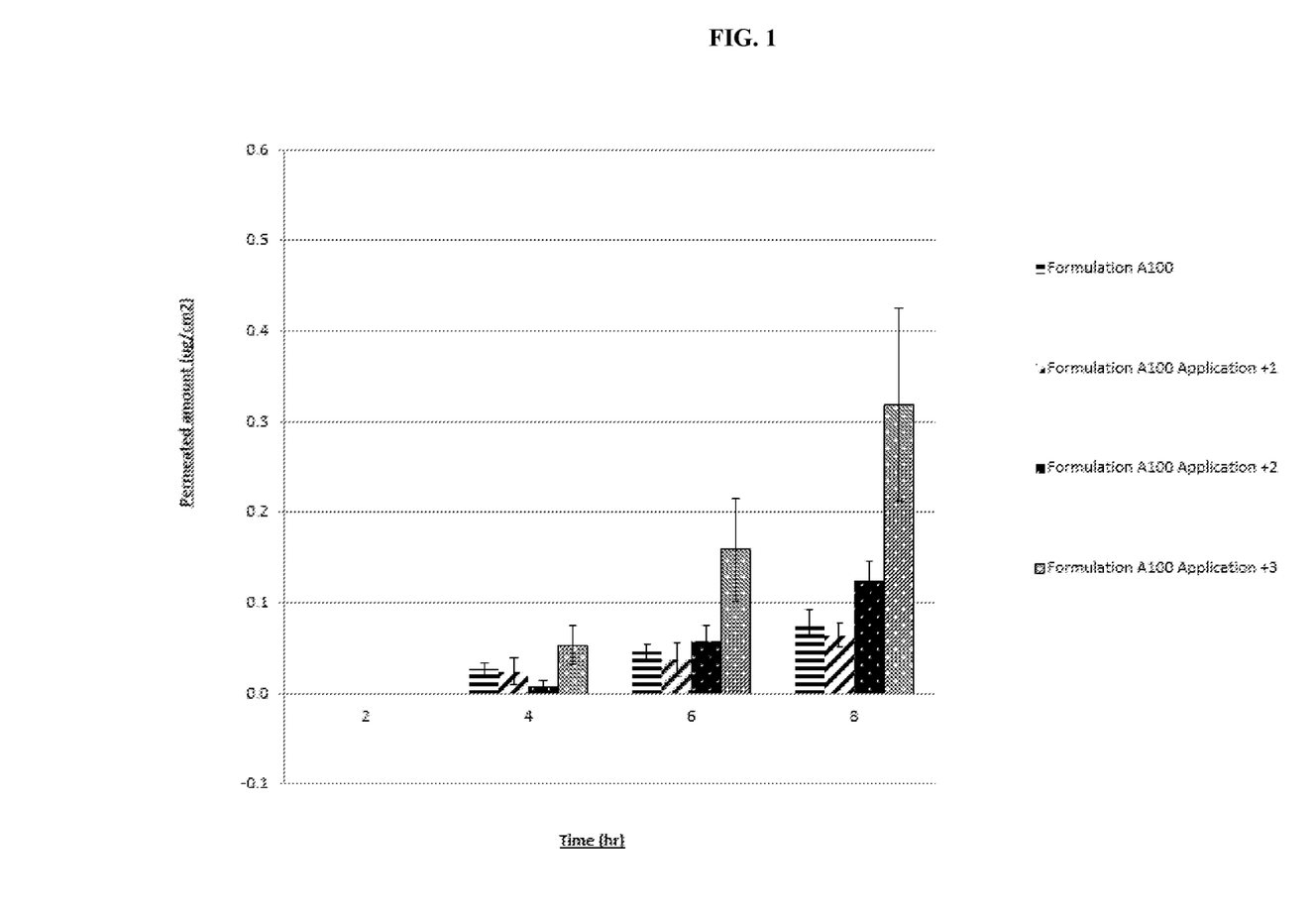
FIG. 1 depicts permeation results of an exemplary formulation of the present technology through human cadaver skin using Franz diffusion cells after repeat applications. Results are shown for measurements at 2, 4, 6, and 8 hour time-points.
Figure 2:
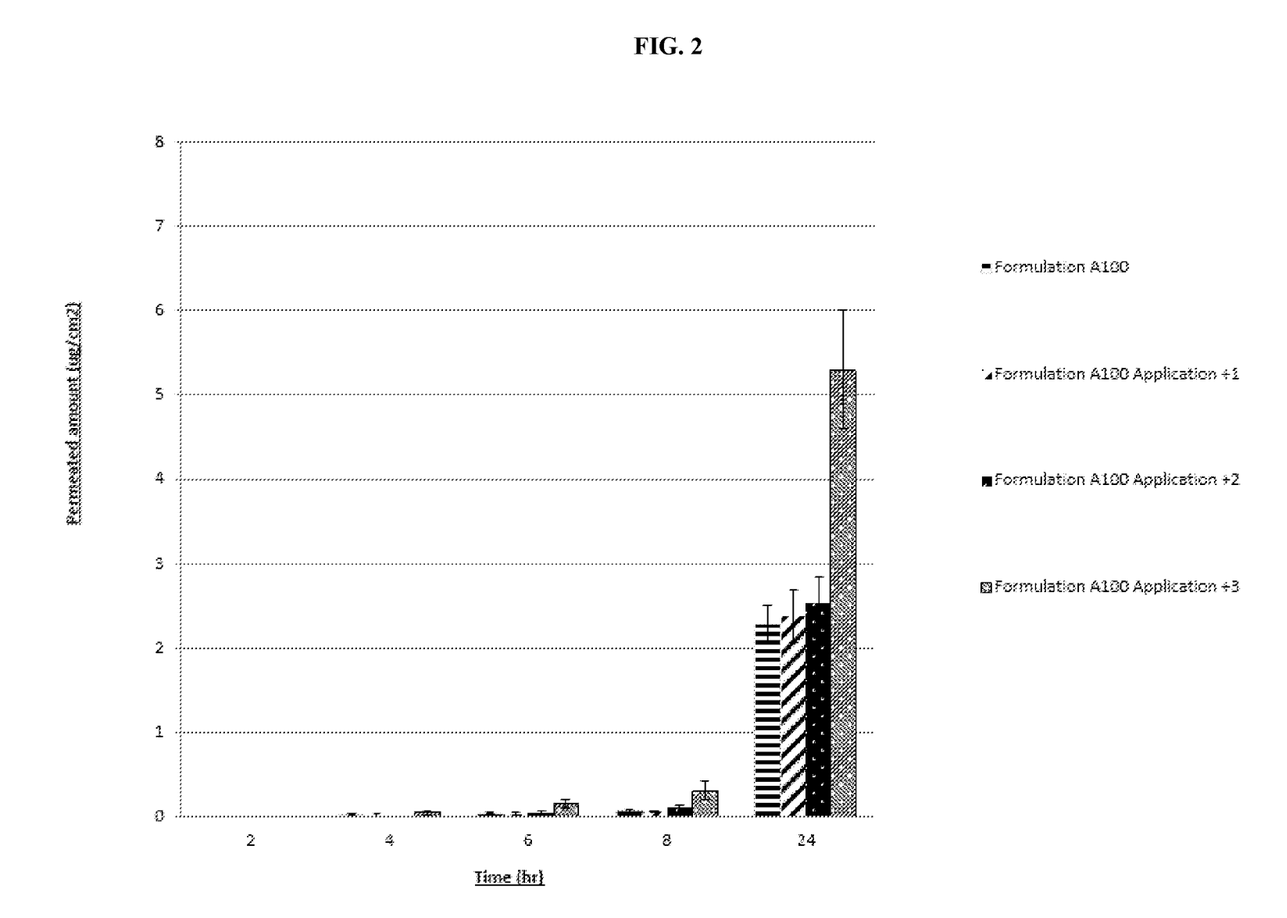
FIG. 2 depicts permeation results of the same exemplary formulation of the present technology of FIG. 1 through human cadaver skin using Franz diffusion cells after repeat applications. Results are shown for measurements at 2, 4, 6, 8 and 24 hour time-points.

Results are shown in FIG. 1 and FIG. 2. Although administration of 3 repeat applications demonstrates the highest permeated amount after 8 hours, the permeated amount remains low (approximately 0.3 μg/cm² or less), as are the permeation amounts for the single application, 1 repeat-application and 2-repeat application (FIG. 1). Unexpectedly, the permeation values display a 16-fold to 30-fold increase after 24 hours (FIG. 2). Lag time was determined to be 3.3 hours. (Lag time is the intercept of steady-state absorption flux straight line with the time line axis which takes place after absorption has started. It reflects the delayed absorption into viable tissue related to the penetration into the stratum corneum. Direct lag time measurement in vivo is not possible but is estimated by extrapolation of the linear portion of the permeation plot to the time axis.)

Example 3. Repeat Application Study—Retention Assessment

Skin samples were assayed to determine the amount of active agent retained in the skin as follows. After 24 hours of the permeation study of Example 2, the skin pieces were first wiped clean with cotton swabs and inspected visually to ensure that no formulation remained. The skin pieces were carefully and quickly wiped twice with Ethanol/water (80:20) impregnated cotton swabs and blotted dry each time with Kimwipes (cellulose cloths). The skins were placed into capped 1.5-dram vials to which 2 ml of ethanol (100%) were added and then sealed with Parafilm (paraffin wax). The vials were stirred overnight at 35° C. to allow the retained active agent to be extracted into ethanol. After cooling to room temperature, the samples were centrifuged and the supernatant was analyzed by HPLC.

Figure 3:
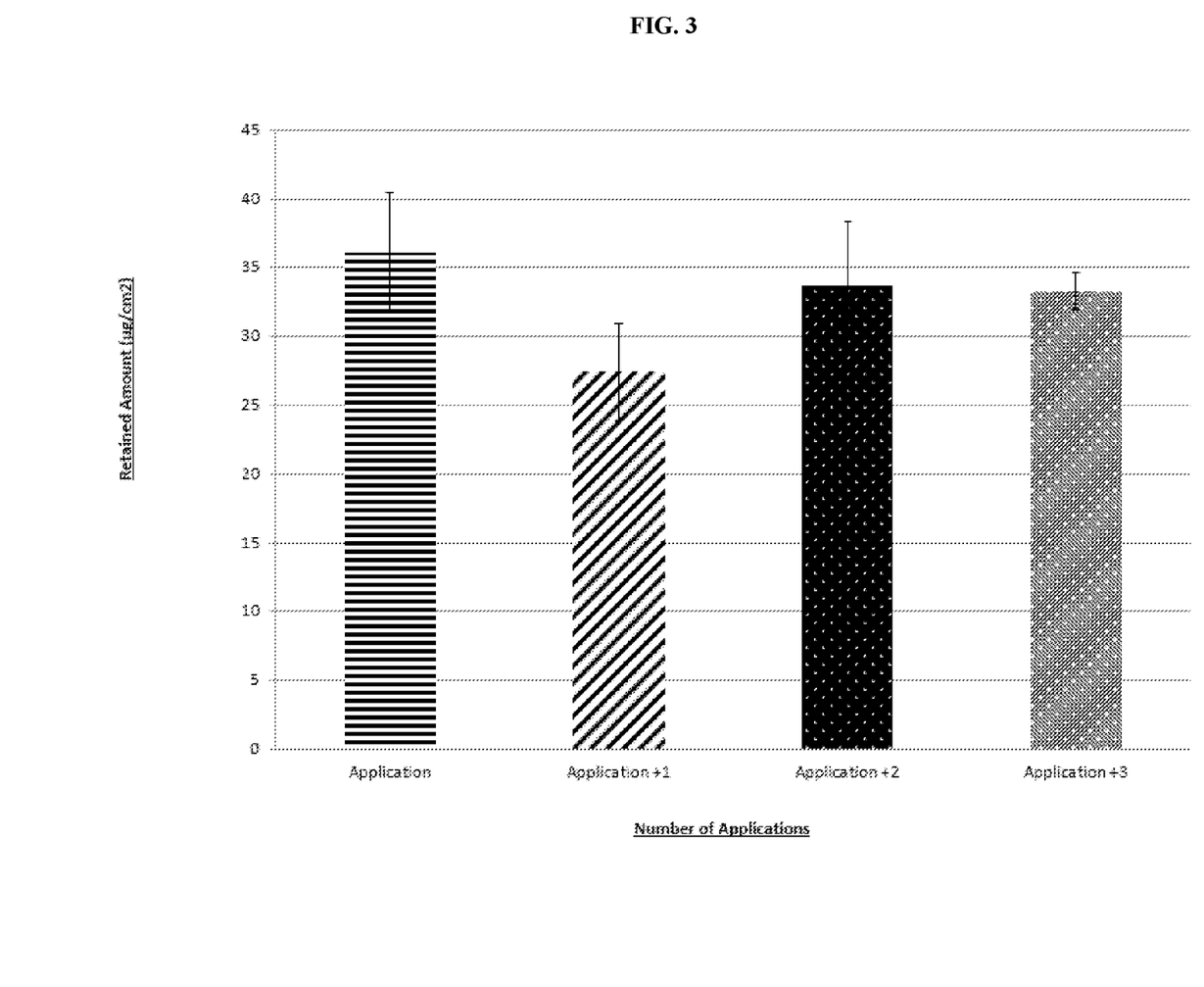
FIG. 3 depicts cannabidiol (CBD) retention results after the 24-hour time-point shown in FIG. 2.

Results are shown in FIG. 3. No significant skin retention differences across the different treatment groups were observed after 24 hours.

Example 4. Comparative Permeation Study

For this study, skin pieces from a human female (66 years old, 155 lbs, back skin, 250 μm thickness), shipped and stored frozen at −20° C. were used, and prepared as described in Example 2.

Five replicates of each formulation were tested versus control (Formulation A100 versus marketed formulation). Each test formulation was applied at a dose of 10 mg and spread uniformly. The Franz cells were maintained at 35° C. and the receptor compartment was continuously stirred with a magnetic stir bar. A sample was taken from each receptor compartment at predetermined time intervals (preferably, 2, 4, 6/8 and 22/24 hour). The samples were assayed by HPLC.

The marketed formulation contained hemp extract (includes cannabidiol), camphor, menthol, beeswax, clove oil, cotton, seed oil, *eucalyptus* oil, jojoba seed oil, peppermint oil, sorbic acid, and tea tree oil.

Figure 4:
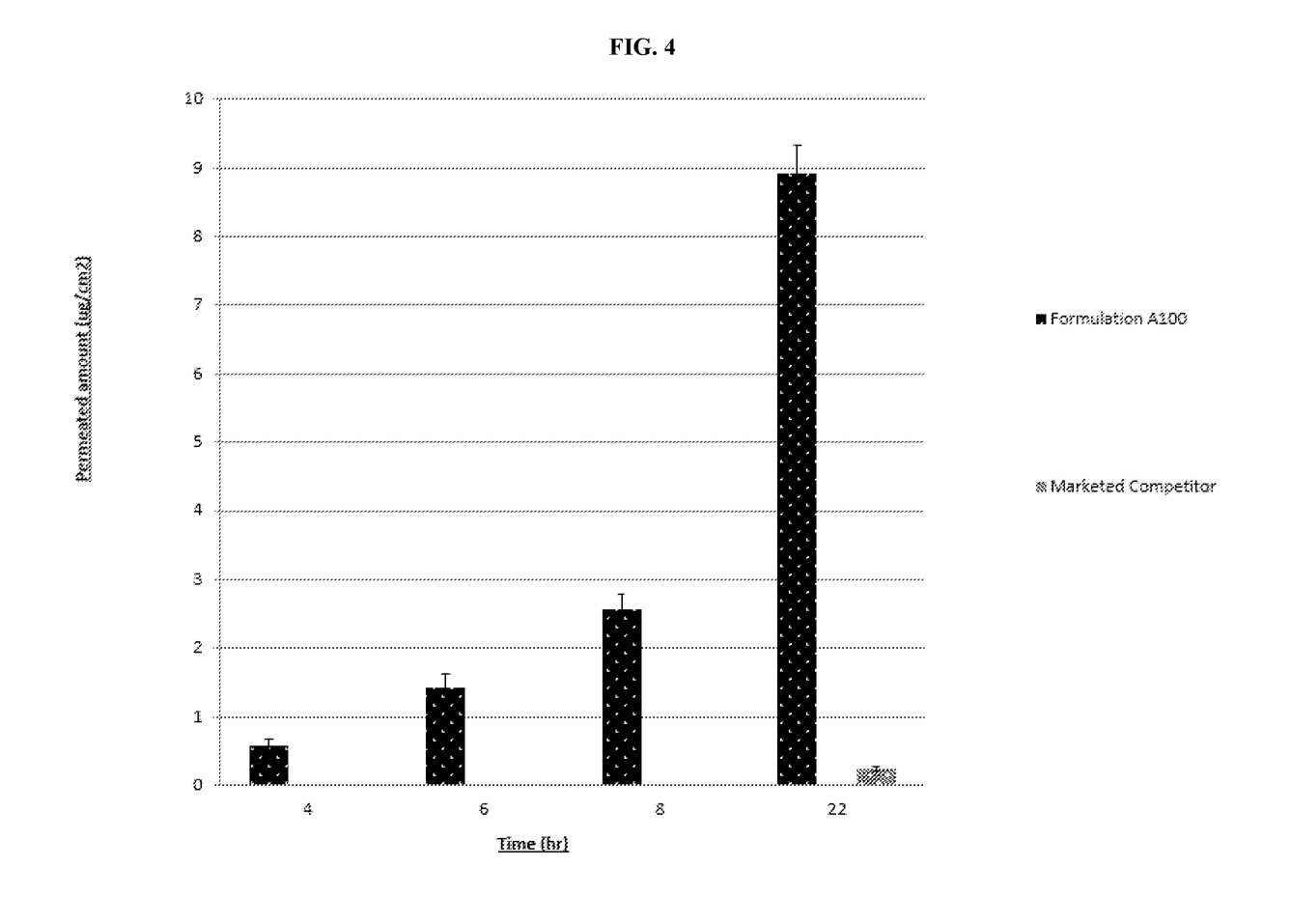
FIG. 4 depicts permeation results of the same exemplary formulation of the present technology of FIG. 1 compared to a marketed formulation (denoted as marketed competitor) through human cadaver skin using Franz diffusion cells. Results are shown for measurements at 4, 6, 8, and 22-hour time-points.

Results are shown in FIG. 4. The marketed formulation did not show any permeation as measured up to 8 hours, and showed a small amount of permeation after 22 hours.

Figure 5:
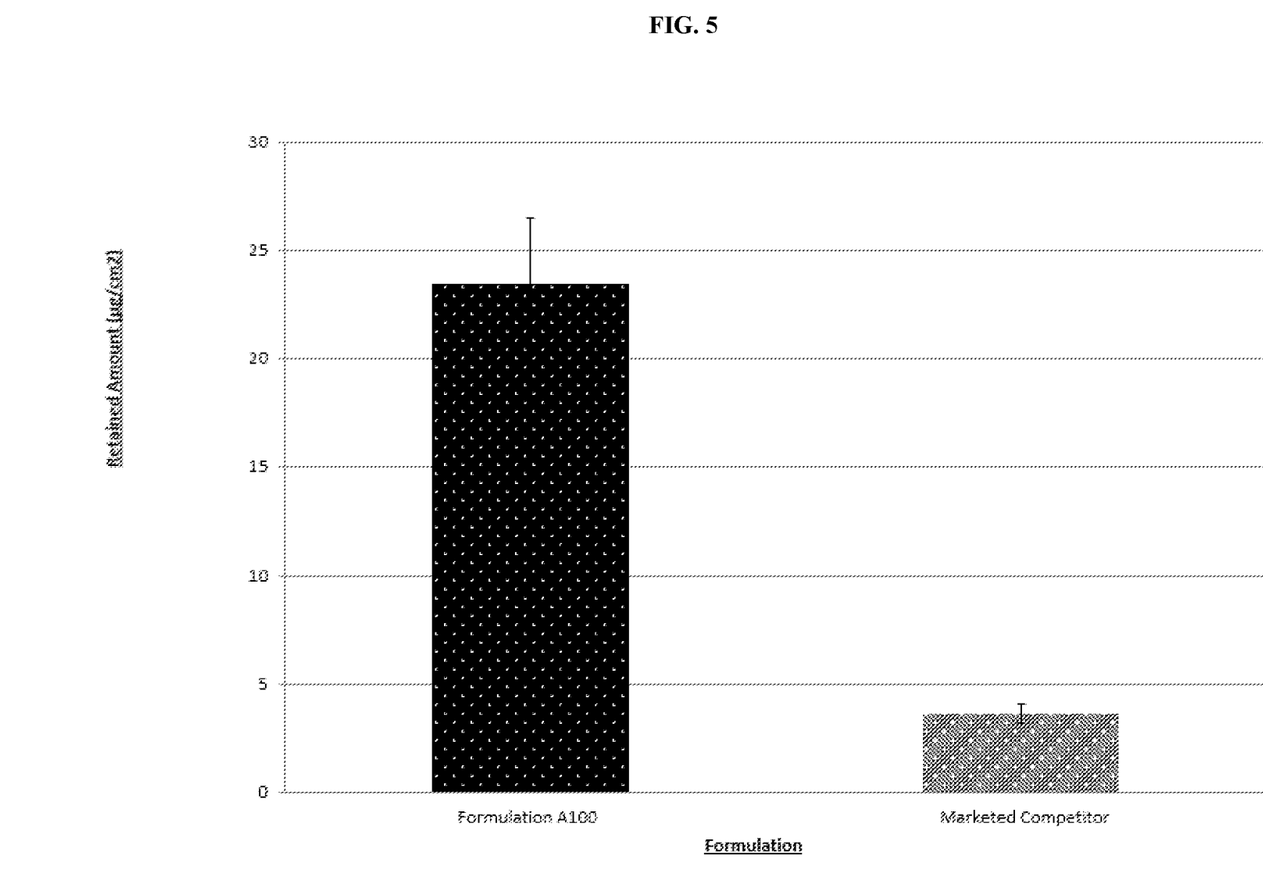
FIG. 5 depicts CBD retention results after the 22-hour time-point shown in FIG. 4.

Retention was assessed as was described in Example 3. Results are shown in FIG. 5. Formulation A100 demonstrated 6-fold higher retention than the marketed formulation after 24 hours.

Example 5. Open Label Experiential Study for Joint and/or Muscle Pain

Figure 6:
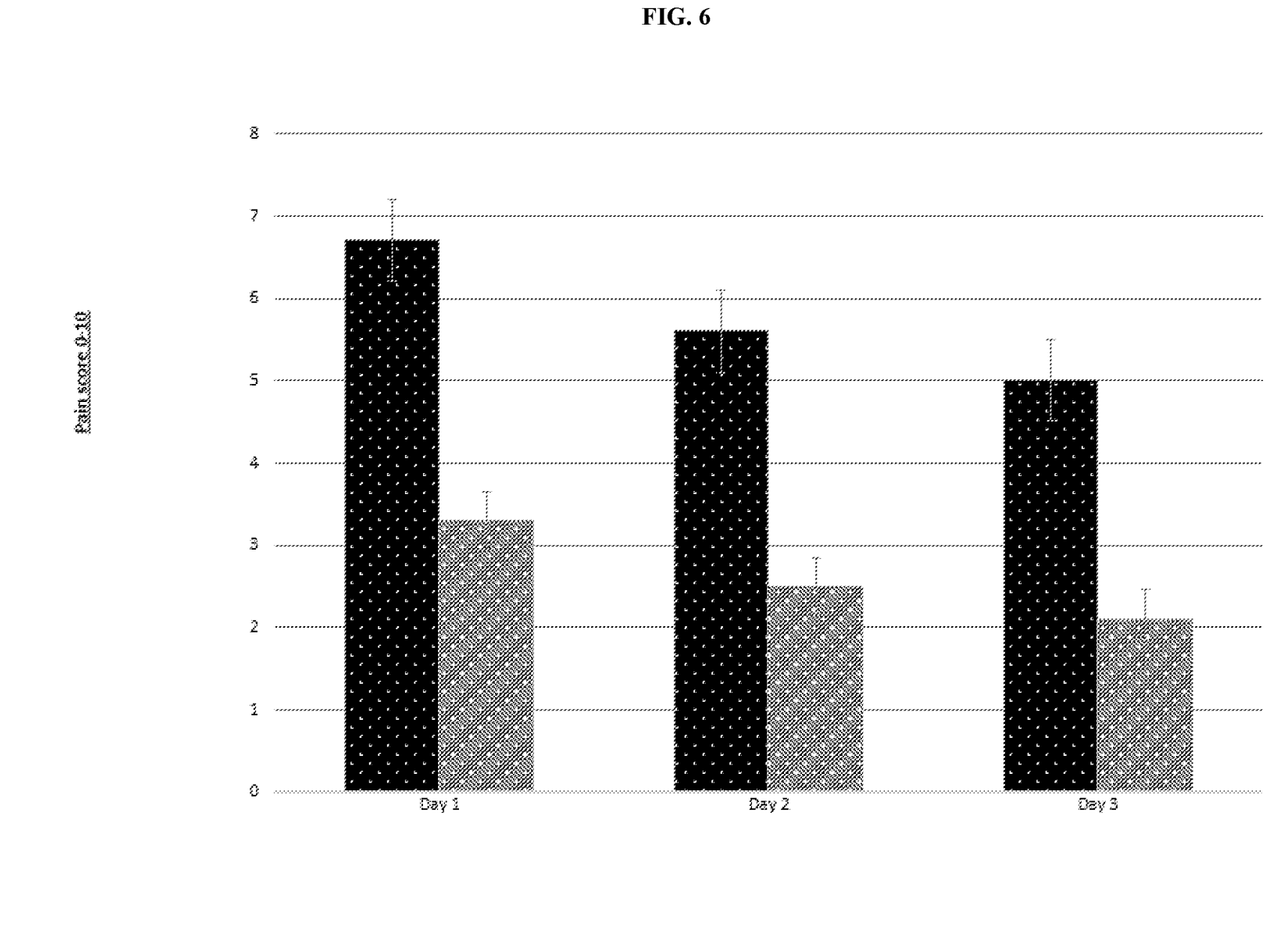
FIG. 6 depicts self-reported pain scores in an open label study for treatment of joint and/or muscle pain.

Female subjects between the age of 40-75 years old administered Formulation A100 (formulation of Example 1) several times daily to treat joint and/or muscle pain. Each subject completed a questionnaire (designed to record the efficacy of Formulation A100 and various sensory experiences) before and after each use of Formulation A100 for 3 consecutive days. Interim results (n=32) regarding efficacy as recorded by the questionnaires are presented in FIG. 6. Overall pain scores decreased by 4.6 points, an improvement of 69%. Subjects reported that Formulation A100 applied smoothly and absorbed quickly into the skin without leaving a residue.

Example 6. Formulation of Cannabidiol (Formulation A110)

| Constituents | Concentration (% w/w) |
|---|---|
| cannabigerol | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

Example 7. Formulation of Cannabidiol (Formulation A120)

| Constituents | Concentration (% w/w) |
|---|---|
| cannabichromene | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

Example 8. Formulation of Cannabidiol (Formulation A130)

| Constituents | Concentration (% w/w) |
|---|---|
| cannabinol | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

Example 9. Formulation of Cannabidiol (Formulation A140)

| Constituents | Concentration (% w/w) |
|---|---|
| cannabitriol | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

Example 10. Formulation of Cannabidiol (Formulation A150)

| Constituents | Concentration (% w/w) |
|---|---|
| cannabidiolic acid | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

Example 11. Formulation of Cannabidiol (Formulation A160)

| Constituents | Concentration (% w/w) |
|---|---|
| cannabigerolic acid | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

Example 12. Formulation of Cannabidiol (Formulation A170)

| Constituents | Concentration (% w/w) |
|---|---|
| cannabidivarin | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

Example 13. Formulation of Cannabidiol (Formulation A180)

| Constituents | Concentration (% w/w) |
|---|---|
| beta caryophyllene | 0.2 |
| diethylene glycol monoethyl ether | 18 |
| cross-linked polyacrylic acid polymer (CARBOPOL ® Ultrez 30) | 1 |
| triethanolamine | 0.3 |
| disodium EDTA dihydrate | 0.05 |
| phenoxyethanol | 0.5 |
| deionized water | q.s. |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A transdermal formulation consisting of from about 0.05% w/w to about 50% w/w microencapsulated cannabidiol dispersed in a pharmaceutically acceptable carrier consisting of:
    from about 3% w/w to about 30% w/w penetration enhancer selected from the group consisting of diethylene glycol monoethyl ether, lauryl alcohol, dimethyl sulfoxide (DMSO), dimethyl acetamide, N-methyl pyrrolidone, oleic acid, azone, urea, terpene, and combinations of any two or more thereof,
    from about 0.8% w/w to about 1.3% w/w thickening agent selected from the group consisting of cross-linked polyacrylic acid polymers; hydroxyethylcellulose, ethyl cellulose, hydroxypropyl cellulose, carboxymethyl cellulose, sodium carboxymethyl cellulose; xanthan gum, locust beam gum, guar gum; alginic acid; PEMULEN™ (a copolymer of acrylic acid and $C_{10}$-$C_{30}$ alkyl acrylate cross-linked with allyl pentaerythritol); and combinations of any two or more thereof,
    from about 0.25% w/w to about 6% w/w buffering agent selected from the group consisting of triethanolamine, potassium hydroxide, cocoamidodiethylamine, and combinations of any two or more thereof,
    from about 0.05% w/w to about 0.08% w/w sequestering agent selected from the group consisting of EDTA and salts and solvates thereof; citric acid; tartaric acid; and combinations of any two or more thereof,
    from about 0.4% w/w to about 0.8% w/w of preservative selected from the group consisting of phenoxyethanol, ethylhexylglycerine, hydantoin, sorbic acid, anisic acid, and combinations or any two or more thereof, and
    up to about 95.45% w/w of deionized water;
    wherein all percentages are based on the total weight of the formulation;
    wherein the transdermal formulation is a semi-solid formulation selected from the group consisting of a gel, a lotion, a cream, an ointment, a serum, and a foam.

2. The formulation of claim 1, wherein the microencapsulated cannabidiol comprises cannabidiol encapsulated within liposomes.

3. The formulation of claim 1, consisting of
    about 0.20% w/w microencapsulated cannabidiol,
    about 18% w/w diethylene glycol monoethyl ether,
    about 1% w/w cross-linked polyacrylic acid polymer,
    about 0.3% w/w triethanolamine,
    about 0.5% w/w phenoxyethanol,
    about 0.05% w/w disodium EDTA dihydrate, and
    q.s. deionized water.

4. A method of treating musculoskeletal pain and/or inflammation in a subject in need thereof, the method comprising topically administering to one or more regions of skin on the subject a therapeutically effective amount of a transdermal formulation of claim 1.

5. The method of claim 4, wherein the transdermal formulation is administered by topical application to the region of skin on the subject without microneedle delivery.

6. The method of claim 4, wherein the transdermal formulation is administered once every hour for an initial period of three hours for a total of four applications and then subsequently administered 3-4 times per day.

7. The method of claim 4, wherein the musculoskeletal pain and/or inflammation is located at one or more of the foot, ankle, knee, hip, hand, wrist, elbow, neck, scalp, back, chest, abdomen, shoulder, arm, or leg, of the subject.

8. A method for relieving pain associated with osteoarthritis of one or more joints in a subject in need thereof, the method comprising topically administering a therapeutically effective amount of a transdermal formulation of claim 1 to one or more regions of skin covering the one or more joints on the subject.

9. The method of claim 8, wherein the one or more joints are located at one or more of the foot, ankle, knee, hip, hand, wrist, elbow, neck, back, or shoulder of the subject.

10. The method of claim 8, wherein the transdermal formulation is administered by topical application to the region of skin on the subject without microneedle delivery.

11. The method of claim 8, wherein the transdermal formulation is administered once every hour for an initial period of three hours for a total of four applications and then subsequently administered 3-4 times per day.

12. The formulation of claim 1, wherein the formulation exhibits a lag effect wherein, following four consecutive hourly applications of the formulation to skin, the amount of cannabidiol delivered through the skin after 21 hours is greater than the amount delivered through the skin after 5 hours, as assessed in an in vitro permeation study using human cadaver skin.

* * * * *